US005817351A

United States Patent [19]
DeWille et al.

[11] Patent Number: 5,817,351
[45] Date of Patent: *Oct. 6, 1998

[54] CALCIUM FORTIFIED LOW PH BEVERAGE

[75] Inventors: Normanella Torres DeWille, Columbus; Michael Allen Chandler, Gahanna; Terrence Bruce Mazer, Reynoldsburg; Robert John Ragan, Gahanna; Gregory Allan Snowden, Westerville; Maureen Elizabeth Geraghty, Columbus; Catherine Dubinin Johnson, Dublin, all of Ohio

[73] Assignee: Abbott Laboratories, Abbott Park, Ill.

[*] Notice: The term of this patent shall not extend beyond the expiration date of Pat. No. 5,597,595.

[21] Appl. No.: 789,452

[22] Filed: Jan. 27, 1997

Related U.S. Application Data

[63] Continuation-in-part of Ser. No. 418,391, Apr. 7, 1995, Pat. No. 5,597,595.

[51] Int. Cl.⁶ .............................. A23L 1/303; A23L 1/304
[52] U.S. Cl. ................................ 426/74; 426/72; 426/73; 426/573; 426/590; 426/601; 426/650
[58] Field of Search .................................. 426/73, 74, 72, 426/590, 573, 601, 650

[56] References Cited

U.S. PATENT DOCUMENTS

| | | |
|---|---|---|
| 3,949,098 | 4/1976 | Bangert . |
| 3,958,017 | 5/1976 | Morse et al. . |
| 4,252,797 | 2/1981 | Rosenthal . |
| 4,497,800 | 2/1985 | Larson et al. . |
| 4,737,375 | 4/1988 | Nakel et al. . |
| 4,740,380 | 4/1988 | Melachouris et al. . |
| 4,786,510 | 11/1988 | Nakel et al. . |
| 4,867,989 | 9/1989 | Silva et al. . |
| 4,929,774 | 5/1990 | Fukamachi et al. . |
| 4,956,191 | 9/1990 | Ueda et al. . |
| 4,992,282 | 2/1991 | Mehansho et al. . |
| 5,221,668 | 6/1993 | Henningfield et al. . |
| 5,260,279 | 11/1993 | Greenberg . |
| 5,401,524 | 3/1995 | Burkes et al. . |
| 5,438,042 | 8/1995 | Schmidl et al. . |
| 5,456,926 | 10/1995 | Hill et al. . |
| 5,480,661 | 1/1996 | Ellis et al. . |
| 5,500,232 | 3/1996 | Keating .................................. 426/599 |
| 5,516,535 | 5/1996 | Heckert et al. ......................... 426/599 |
| 5,550,232 | 8/1996 | Keating . |
| 5,597,595 | 1/1997 | DeWille et al. . |
| 5,609,897 | 3/1997 | Chandler et al. ....................... 426/599 |

FOREIGN PATENT DOCUMENTS

| | | |
|---|---|---|
| A 0 497 287 | 5/1982 | European Pat. Off. . |
| A 0 265 099 | 4/1988 | European Pat. Off. . |
| 0486425 | of 1992 | European Pat. Off. . |
| A 0 560 989 | 9/1993 | European Pat. Off. . |
| A 0 102 663 | 3/1998 | European Pat. Off. . |
| B 11 23 084 | 1/1962 | Germany . |
| 0210024 | of 1984 | Japan . |
| A 590 809 | 7/1947 | United Kingdom . |
| 1118606 | 3/1968 | United Kingdom . |
| 1118608 | 3/1968 | United Kingdom . |
| 2196523 | 5/1988 | United Kingdom . |
| WO 91/19692 | 12/1991 | WIPO . |
| WO 92/19251 | 11/1992 | WIPO . |
| WO 92/21355 | 12/1992 | WIPO . |
| 95/05808 | 2/1995 | WIPO . |

OTHER PUBLICATIONS

Woodroof, et al., Beverages: Carbonated and Noncarbonated, AVI Publishing, 1974, pp. 143–146.

MeLillo, "Physical Factors Governing the Stabilization of Cloudy Beverages", Food Products Development, Jun. 1977, pp. 108–110.

Data From the National Health Survey, Series II, No. 231, DHHS Pub. No. (PHS) 83–1681, p.20 (1983).

Kelley, et al., "Effect of Meal Composition on Calium Absorption: Enhancing Effect of Carbohydrate Polymer," Gastroenterology, 87:596–600 (1984).

Bei, et al., "Glucose Polymer Increases and Equal Calcium Magnesium and Zinc Absorption in Humans," American Journal Clinical Nutrition, 44:244–247 (1986).

Beuchat, Food and Beverage Mycology, Van Nostrand Reihhold, 1987, pp. 120–122.

Smith, et al., "Calcium Absorption from a New Calcium Delivery System (CCM)", Calcified Tissue International, 41:351–352 (1987).

"Nationwide Food Consumption Survey, Continuing Survey of Food Intakes of Individuals," USDA NFCS, CFS II Report No. 86–3 (1988) pp. 62 and 75.

Spencer, et al., "Do Protein and Phosphorous Cause Calcium Loss?" Journal of Nutrition, 118:657–660, (1988).

Champagne, "Low Gastric Hydrochloric Acid Secretion and Mineral Bioavailability," Advances in Experimental Medicine and Biology, 249:173–184 (1989).

Mehansho, et al., "Calcium Bioavailability and Iron Calcium Interaction In Orange Juice", Journal of the American College of Nutrition, 8(1):61–68 (1989).

Churella, et al, Relative Calcium (Ca) Bioavailability of Ca Salts Used In Infant Formulas,: The FASEB Journal, 4(3):A788 (1990).

Hanning, et al, "Efficacy of Calcium Gycerophosphate vs. Conventional Mineral Salts for Total Parenteral Nutrition in Low–Birth–Weight Infants: A Randomized Clinical Trial", American Journal Of Clinical Nutrition, 54:903–908 (1991).

Draper, et al., "Calcium Glycerphosphate as a Source of Calcium and Phosphorous in Total Parenteral Nutrition Solutions", Journal Of Parenteral And Enteral Nutrition, 15(2):176–180 (1991).

Sakhee, et al., "Calcium citrate without aluminum antacids does not cause aluminum retention in patients with functioning kidneys", Bone and Mineral, 20:87–97 (1993).

(List continued on next page.)

Primary Examiner—Helen Pratt
Attorney, Agent, or Firm—Thomas D. Brainard; J. Michael Dixon

[57] ABSTRACT

Liquid beverages for supplementation of dietary calcium are disclosed. The beverages of this invention use calcium glycerophosphate as the source of calcium, acidulants, vitamin C and optionally, vitamin D.

12 Claims, No Drawings

OTHER PUBLICATIONS

Wardlaw, "Putting Osteoporosis in Perspective", Journal Of The American Dietetic Association, 93(9): 1000–1006 (1993).

Journal of the American Medical Association, 272 (24): 1942–1948 (1994).

Whiting, "Safety of Some Calcium Supplements Questioned", Nutrition Reviews, 52(3):95–97 (1994).

Federal Register, 58(3):2665–2681 (1993).

56 FR 60689–60725 (1991).

"Optimal Calcium Intake", Journal Of The American Medical Association, 272,(24): 1942–1948 1994).

National Institute of Health (NIH) Conference on Optimal Calcium Intake, held Jun. 6–8, 1994.

"Rote Liste 1987", Bundesverband Der Pharmazeutischen Industrie E.V., Editio Cantor, Aulendorf/Württ. XP002018074, Numbers 83 103 and 83 105.

Database WPI, Section Ch, Week 8618, Derwent Publication Ltd., London, GB; Class D13. AN 96–117187, XP002018075 & JP, A, 61 058 560 (Nippon Oils & Fats KK), 25 Mar. 1986—See Abstract.

Physicians Desk Reference, 19th Edition, Publlished 1965, P 1015.

Physicians Desk Reference, 48th Edition, Published 1994, p. 115.

CALCIUM FORTIFIED LOW PH BEVERAGE

CROSS-REFERENCE TO RELATED APPLICATIONS

This application is a continuation-in-part of U.S. application Ser. No. 08/418,391 filed Apr. 7, 1995, now U.S. Pat. No. 5,597,595 issued Jan. 28, 1997.

TECHNICAL FIELD

The present invention relates to a liquid nutritional product which has a low pH and is fortified with calcium and vitamin C to meet 50%, most preferably, 100%, of the adult RDI for vitamin C in a twelve ounce (355 ml) serving and from 30–50% of the adult RDI for calcium in a 12 ounce serving. Most preferably, the beverage of this invention contains 30–50% of the RDI for calcium and 100% of the RDI for vitamin C in 355 ml..

BACKGROUND OF THE INVENTION

Calcium is an essential nutrient; it is a major component of mineralized tissues and is required for normal growth and development of the skeleton and teeth. Over the last decade, calcium has enjoyed increased attention due to its potential role in the prevention of osteoporosis. Osteoporosis affects more than 25 million people in the United States and is the major underlying cause of bone fractures in postmenopausal women and the elderly. "Optimal Calcium Intake", JOURNAL OF THE AMERICAN MEDICAL ASSOCIATION, 272(24): 1942–1948 (1994).

As used herein "osteoporosis" refers to a reduction in the amount of bone mass. Two important factors influencing the occurrence of osteoporosis are optimal peak bone mass attained in the first two to three decades of life and the rate at which bone mass is lost in later years. Adequate calcium intake is critical to achieving optimal peak bone mass and modifies the rate of bone mass loss associated with aging. Wardlaw, "Putting Osteoporosis in Perspective", JOURNAL OF THE AMERICAN DIETETIC ASSOCIATION, 93(9): 1000–1006 (1993).

Calcium requirements vary throughout an individual's lifetime with greater needs occurring during the period of rapid growth in childhood and adolescence, pregnancy and lactation, and in later adult life. Table 1 presents the optimal calcium requirements or Recommended Daily Intake (RDI) which were established at a National Institute of Health (NIH) Conference on Optimal Calcium Intake, held Jun. 6–8, 1994. "Optimal Calcium Intake", JOURNAL OF THE AMERICAN MEDICAL ASSOCIATION, 272(24):1942–1948, at 1943 (1994). The participants at the NIH Conference considered former Recommended Dietary Allowances (RDA) (10th edition, 1989) for calcium intake as reference levels and used them as guidelines to determine optimal calcium intake in light of new data on calcium-related disorders.

TABLE 1

Optimal Calcium Intakes

| GROUP | OPTIMAL DAILY INTAKE (in mg of calcium) |
|---|---|
| Infants | |
| Birth–6 months | 400 |
| 6 months–1 year | 600 |
| Children | |
| 1–5 years | 800 |
| 6–10 years | 800–1,200 |
| Adolescents/Young Adults | |
| 11–24 years | 1,200–1,500 |
| Men | |
| 25–65 years | 1,000 |
| Over 65 years | 1,500 |
| Women | |
| 25–50 years | 1,000 |
| Over 50 years (postmenopausal) | |
| On estrogens | 1,000 |
| Not on estrogens | 1,500 |
| Over 65 | 1,500 |
| Pregnant and nursing | 1,200–1,500 |

National consumption data indicate most females over the age of eleven, as well as elderly men, consume amounts of calcium below recommended levels. "Nationwide Food Consumption Survey, Continuing Survey of Food Intakes of Individuals", USDA NFCS, CFS II Report No. 86–93 (1988). According to the Second National Health and Nutrition Examination Survey, the median daily calcium intake for women in the United States was 574 mg. DIETARY INTAKE SOURCE DATA: UNITED STATES, 1976–80, Data From the National Health Survey, Series II, No. 231, DHHS Publication No. (PHS), pages 83–1681 (1983).

The preferred approach to attaining optimal calcium intake is through dietary sources. Dairy products are the major contributors of dietary calcium because of their high calcium content (e.g. approximately 250–300 mg/8 oz of cow's milk) and frequency of consumption. However, many persons, especially women, prefer to limit their intake of dairy products for several reasons: (a) they dislike the taste of milk/milk products; and/or (b) they have a lactose intolerance; and/or (c) they perceive that some dairy products are too high in fat or protein and may lead to weight gain. A number of calcium-fortified food products are currently available, including fortified juices, fruit drinks, breads and cereals.

To maximize calcium absorption, food selection decisions should include consideration of information on the bioavailability of the calcium contained in the food. Bioavailability (absorption) of calcium from food depends on the food's total calcium content and the presence of components which enhance or inhibit calcium absorption. Bioavailability of minerals in food has been traditionally tested by the balance method, which estimates absorption from the difference between ingested intake and fecal output. This approach works well for many nutrients where the difference between intake and excretion is large, but is less well suited for an element such as calcium. A decline in absorption from 30% to 20% could have profound nutritional significance but would be difficult to detect using the balance method. In contrast, isotopic methods estimate absorption directly from the appearance of the ingested tracer in body fluids. Future clinical evaluations of the bioavailability of calcium from the liquid nutritional product of the present invention will use a state-of-the-art isotope tracer method.

Not all calcium salts are created equally. Calcium salts range from 9% elemental calcium in calcium gluconate to 40% calcium in calcium carbonate. Bioavailability depends on solubility. A new calcium delivery system, Calcium Citrate Malate (CCM) claims to be approximately six-times the solubility of either calcium citrate or calcium malate, both of which are themselves substantially more soluble than calcium carbonate. Smith et al., "Calcium Absorption from a New Calcium Delivery System (CCM)", CALCIFIED TISSUE INTERNATIONAL, 41:351–352 (1987) relates an experiment in humans wherein calcium from CCM was absorbed significantly better than from either calcium carbonate or milk, 38.3% vs. 29.6% and 29.4% respectively. WO 91/19692 discloses a process for making a metastable calcium citrate malate.

The United States Food and Drug Administration (FDA) has advised that, in order for calcium-containing food ingredients in conventional foods or calcium supplement products to be considered eligible to bear the authorized calcium/osteoporosis health claim, they must meet the requirements in §101.14, which include that they have been shown to the FDA's satisfaction to be safe and lawful under the applicable safety provisions of the Act (56 FR at 60699). Of the 36 or more calcium-containing ingredients identified by the agency as currently in use, the FDA advised that only the following 10 compounds had been demonstrated to be safe and lawful for use in a dietary supplement or as a nutrient supplement: calcium carbonate, calcium citrate, calcium glycerophosphate, calcium oxide, calcium pantothenate, calcium phosphate, calcium pyrophosphate, calcium chloride, calcium lactate, and calcium sulfate (56 FR at 60691).

For some individuals, calcium supplements may be the preferred way to obtain optimal calcium intake. Although calcium supplements are available in many salts, calcium carbonate is usually recommended because it contains more elemental calcium per gram than any of the other salts. The disintegration and dissolution characteristics of commercial calcium carbonate preparations, which vary widely, may produce important differences in calcium absorption. Other problems with using large amounts of calcium carbonate is that it can lead to constipation and abdominal distention. When problems arise, calcium lactate or calcium citrate are advised. A popular commercially available calcium supplement is TUMS 500™ which is distributed by SmithKline Beecham, Pittsburgh, Pa., U.S.A. and is labeled as providing 500 mg of elemental calcium (from calcium carbonate) per tablet.

U.S. Pat. Nos. 4,786,510 and 4,992,282 disclose the use of calcium citrate malate in a beverage or dietary supplement fortified with iron.

WO 92/19251 and WO 92/21355 disclose the use of calcium citrate malate in a low pH beverage, and suggests that vitamin D be added to such a beverage along with oil flavors or weighing oil.

EP 0 486 425 A2 discloses a liquid oral nutritional formulation which contains carbohydrates, protein, fat, fiber, calcium, and vitamin D, and has a pH of about 3.5 to 3.9. However, this publication teaches that high amounts of micronutrients such as calcium or magnesium may impair the palatability of the product, and should contain the recommended daily allowance of these nutrients in about one liter of product. A commercially available product in accordance with this patent publication is distributed by Sandoz Nutrition under the trade name CITRISOURCE® and is labeled as providing 570 mg of calcium and 210 IU of vitamin D per liter. By way of comparison, one embodiment of a beverage according to the present invention contains at least 1,408 mg of calcium per liter or 0.14 wt. %.

U.S. Pat. No. 4,737,375 teaches beverage concentrates and beverages having a pH of 2.5 to 6.5, preferably 3.0 to 4.5, which contains calcium derived from calcium citrate malate. The acidulants used in this prior art beverage are chosen from mixtures of citric acid, malic acid and phosphoric acid, and the weight ratio of total acids to calcium is in the range of 4 to 7.

Two commercially available beverages which are labeled as being protected by U.S. Pat. No. 4,737,375 are: (1) Sunny Delight® With Calcium which is distributed by Procter & Gamble, Cincinnati, Ohio 45202 U.S.A.; and (2) HAWAIIAN PUNCH®, DOUBLE C which is distributed by Sundor Brands, Inc., Cincinnati, Ohio 45202 U.S.A.. According to the "Nutrition Facts" on the labels of these commercially available products: (a) neither product contains vitamin D; (b) neither product contains any fat; (c) a 240 mL (8 fluid ounce) serving of Sunny Delight® With Calcium provides 30% of the recommended daily intake (RDI) of calcium; (d) a 240 mL (8 fluid ounce) serving of HAWAIIAN PUNCH®, DOUBLE C provides 15% of the recommended daily intake of calcium; and (e) and a 240 mL (8 fluid ounce) serving of each of these products provides 100% of the recommended daily intake of vitamin C. Per the product labels, these percent daily values are based on a 2,000 calorie diet. Samples of each of these products were tested regarding their pH values: the pH value of the HAWAIIAN PUNCH® DOUBLE C was 3.91; and the pH value of the Sunny Delight® With Calcium was 4.05.

GB 2 196 253 A discloses a beverage containing calcium and vitamin D. A water soluble non-toxic calcium salt is used in a quantity sufficient to provide in the final beverage a calcium ion content of from $1.0 \times 10^{-2}$ to $40 \times 10^{-2}\%$ w/w (0.01–0.4 wt. %).

U.S. Pat. No. 5,597,595 the parent of this application, claims liquid beverage concentrates that contain calcium glycerophosphate as the calcium source and a vitamin D emulsion. The disclosures and teachings of U.S. Pat. No. 5,597,595 are incorporated herein by reference in its entirety.

GB Patent 1,118,606 discloses a dosage unit for oral administration for the treatment of hemorrhoids comprising calcium glycerophosphate, vitamin D, vitamin C, vitamin B and piperazine phosphate.

U.S. Pat. No. 5,500,232 to Keating discloses calcium fortified acid beverages. This patent teaches the calcium source is a combination of calcium hydroxide and calcium glycerophosphate and the acidulant is a combination of citric acid and fumaric acid.

SUMMARY OF THE INVENTION

In general this invention relates to liquid, ready to consume low pH beverages that provide at least 30%, more preferably 50% of the RDI for calcium and at least 50%, most preferably 100% of the RDI for vitamin C in one serving (12 oz or 355 ml.) One aspect of this invention resides in the discovery that high levels of calcium can be supplied through the use of calcium glycerophosphate in a low pH (2.8 to 4.6) beverage without product stability problems and unpleasant flavors.

Thus, there is disclosed a liquid beverage comprising water, calcium glycerophosphate, vitamin C and an acidulant, the beverage has a pH of from about 2.8 to 4.6 and wherein the beverage contains from about 7.2 to 18% by wt. calcium on a dry weight basis. The beverage may also contain vitamin D that is supplied in the form of an emulsion which comprises vitamin D, vegetable oil and a non-hydrolyzed gum selected from gum arabic, gum tragacanth and xanthan gum. The vegetable oil is preferably selected from corn oil and partially hydrogenated soybean oil.

The acidulants used to lower the pH of the beverage can be those commonly used in the food and beverage industry to impart tart and/or sour tastes. A combination of citric and lactic acids are preferred. More preferred is a 75% by weight lactic acid/25% acetic acid acidulant. The beverage of this invention may also contain ascorbic acid, preservatives such as potassium benzoate, flavoring agents and sweeteners. The preferred sweetener is aspartame as it demonstrates a synergistic effect with CaGP in providing a pleasant taste and mouth feel to the inventive beverage. Other natural and artificial sweeteners can be used, for example acesulfame K.

In a preferred embodiment of the invention the beverage consists essentially of water; 10–18% by wt. calcium on a dry weight basis, said calcium is derived from calcium glycerophosphate; vitamin C; an acidulant mixture comprising 75% by wt. citric acid and 25% by wt. lactic acid; a preservatives; sweeteners and flavoring agents; said beverage has a pH of about 3.1 to about 4.0 and provides at least 50% of the RDI for calcium and vitamin C for an adult in about 355 ml.

If the RDI for calcium is 1000 mg/day for post menopausal women over 50 years of age and the inventive beverage supplied 100% of the calcium RDI in one service, then the beverage will contain 5.91 g of CaGP per 355 ml (12 oz.). The same beverage may also provide 100% of the RDI for vitamin C (RDI=60 mg/day) in one serving, thus it would contain 60 mgs of ascorbic acid per 355 ml. In similar fashion, if the beverage according to this invention were designed to provide 30% of the RDI for calcium and vitamin C in one serving, it would contain 1.777 g of CaGP and 18 mg of ascorbic acid per 355 ml. A beverage supplying 50% of the RDI for calcium and vitamin C in one serving would contain 2.96 g of CaGP and 30 mg of ascorbic acid per 355 ml of beverage. In an additional embodiment of the invention, the beverage contains at least 120 IU of vitamin D per 355 ml of beverage.

Selection of Ingredients Used in Practicing the Invention

The present invention provides high levels of calcium in a carbonated or a noncarbonated beverage. As used herein and in the claims the terms "liquid nutritional product" and "beverage" are understood to be synonymous. As used herein and in the claims a "low pH beverage" is understood to refer to a beverage having a pH of less than 4.6. Beverages were manufactured by blending the beverage components with water. Some beverages were then carbonated and filled into standard 12 ounce soda aluminum cans. (Soda aluminum cans are coated in accordance with accepted industry standards to substantially reduce migration of aluminum into the contents of the can.)

Calcium Source. As used herein and in the claims the term "calcium" used alone refers to elemental calcium, the term "calcium salt" refers to a chemical composition containing elemental calcium, and "calcium source" refers to calcium and/or a calcium salt. The calcium salt used in the present invention is Calcium Glycerophosphate (CaGP) which is generally recognized as safe (GRAS) by the United States Food and Drug Administration (FDA) (21 CFR 170.3).

Calcium glycerophosphate (CaGP) can be described as a white, odorless, almost tasteless powder. Its solubility in water increases in the presence of citric and lactic acids, as stated in the Merck Index. The CaGP used herein was FCC III grade and was produced by Dr. Paul Lohman GmbH, Emmerthal, Germany and distributed by Gallard Schlesinger Industries, Inc., Carle Place, N.Y., 11514, USA.

Another reason for selecting CaGP is its excellent calcium bioavailability. Churella et al., "Relative Calcium (Ca) Bioavailability Of Ca Salts Used In Infant Formulas", THE FASEB JOURNAL, 4(3):A788 (1990) reports a study which determined the calcium bioavailability of four calcium salts. Rats were fed various diets containing different calcium salts for three weeks. At the end of the study, the right femur was removed and tested for calcium. As compared to a control, the relative calcium bioavailability was as follows: tricalcium phosphate 110%, calcium citrate 110% and CaGP 106%. Furthermore, studies reported by Hanning et al, "Efficacy of Calcium Glycerophosphate vs. Conventional Mineral Salts for Total Parenteral Nutrition in Low-Birth-Weight Infants: A Randomized Clinical Trial", AMERICAN JOURNAL OF CLINICAL NUTRITION, 54:903–908 (1991), and Draper et. al., "Calcium Glycerophosphate as a Source of Calcium and Phosphorous in Total Parenteral Nutrition Solutions", JOURNAL OF PARENTERAL AND ENTERAL NUTRITION, 15(2):176–180 (1991) showed in low birth weight infants and piglets, respectively, that CaGP is as effective as calcium gluconate as a source of calcium in total parenteral nutrition (TPN) solutions and could be used to prevent under mineralized bones in low birth weight infants.

Yet another reason for selecting CaGP was its high solubility which facilitates a larger calcium intake per serving. A number of calcium salts were evaluated for their functionality in the liquid nutritional product of the present invention: dicalcium phosphate, monocalcium phosphate, calcium chloride, tricalcium phosphate, calcium citrate, calcium carbonate, CaGP, and D-gluconic acid (hemicalcium salt). Aqueous solutions containing 500 mg of calcium per 240 mL (8 oz.) serving (2110 ppm) were prepared and the pH was adjusted to pH 3.5 and pH 5.0. Results indicated that solubility of calcium salts varied and only calcium carbonate, calcium chloride, CaGP, and D-Gluconic acid, remained soluble at pH 3.5 for at least one month. In this evaluation solubility was determined by a visual examination. At pH 5.0 all samples formed crystals over time. The results of this solubility study are presented in Table 2.

TABLE 2

Solubility Of Calcium Sources

| Salt | At Time of Manufacture | | 1 MONTH | |
| --- | --- | --- | --- | --- |
|  | pH 3.5 | pH 5.0 | pH 3.5 | pH 5.0 |
| Dicalcium Phosphate | insoluble | insoluble | insoluble | insoluble |
| Monocalcium Phosphate | insoluble | insoluble | insoluble | insoluble |
| Calcium Chloride | soluble | soluble | soluble | insoluble |
| Tricalcium Phosphate | insoluble | insoluble | insoluble | insoluble |
| Calcium Citrate | insoluble | insoluble | insoluble | insoluble |
| Calcium Carbonate | soluble | partially soluble | soluble | insoluble |
| CaGP | soluble | soluble | soluble | insoluble |
| D-Gluconic-Acid* | soluble | soluble | soluble | partially Soluble |

*Hemicalcium salt

Experiments were repeated with calcium carbonate, CaGP, and calcium chloride in a complete liquid nutritional product matrix, i.e., in conjunction with aspartame, a flavor system and vitamin C. The pH range evaluated was 3.5–4.5. At the lower end of the pH range all calcium sources were soluble at time of manufacture. After one month it was observed that as the pH increased, calcium carbonate formed crystals. In addition, it appeared that the CaGP had a synergistic effect with aspartame regarding sweetness. Calcium chloride was completely soluble throughout the pH range but its bitter flavor made it unacceptable for the liquid nutritional product of the present invention. Calcium lactate was evaluated in subsequent experiments. Although its solubility was excellent it provided astringent and mineral salt-type notes to the taste of the beverage that made it undesirable.

Still another reason for selecting CaGP is the fact that a beverage matrix containing this calcium salt requires the addition of less acid to achieve a pH below 4.0. Acidity is desired in the liquid nutritional product of the present invention for several reasons such as: to maintain the calcium salt solubility, to complement flavor, to control microbial growth, and to enhance the role of preservatives, specifically potassium benzoate or sodium benzoate. On the other hand, too much acidity can result in increased tartness and sourness that make the product undesirable from a sensory point of view. When calcium salts are added to a liquid nutritional product, the solution resists changes in pH and more acid is needed to bring down the pH than in commercially available beverages with no calcium fortification.

Aqueous solutions of various calcium salts were prepared to deliver 500 mg of elemental calcium per 12 oz. (355 mL) serving (1408 ppm) and the pH adjusted to pH 3.5 with citric acid. Titratable acidity was determined by measuring the amount of 0.1N NaOH needed to raise the pH to 8.3 in a 40 g sample containing 1,409 mg/Kg of a calcium source. The results presented in TABLE 3 indicate that, with the exception of calcium chloride, CaGP was the calcium salt that had the lowest titratable acidity. Titratable acidity is an indication of the total acidity of a beverage.

TABLE 3

Titratable Acidity Of Calcium Sources

| Calcium Source | Titratable acidity mL of 0.1 NaOH |
| --- | --- |
| Calcium Chloride | 0.7 |
| CaGP | 43.5 |
| Calcium Lactate | 47.1 |
| Tricalcium Phosphate | 48.6 |
| Calcium Citrate Malate | 53.2 |
| Calcium Citrate | 57.5 |
| Calcium Hydroxide | 60.6 |
| Calcium Carbonate | 61.4 |

CaGP, when dissolved in water, dissociates readily to provide "free" calcium ions and protonated glycerophosphate species. Acid-base buffering by monoprotonated glycerophosphate is effective only within the pH range from 4.1 to 8.1, and thus, CaGP exhibits insignificant buffering capacity at pH=3.6. On the other hand, anions, such as malate, tartrate, propionate or succinate, do provide buffer capacity at pH=3.6, and accordingly require more base or acid than CaGP for final adjustment of pH.

Yet another reason for selecting CaGP is the low aluminum content in commercially available CaGP. It has been theorized that chronic use of calcium supplements which have significant aluminum contents may constitute unnecessary metal exposure. Whiting, "Safety of Some Calcium Supplements Questioned", NUTRITION REVIEWS, 52(3):95–97 (1994). The aluminum content of some calcium sources is presented in TABLE 4.

TABLE 4

Aluminum Content Of Calcium Sources

| Calcium Source | Aluminum Content in parts per million ppm) |
| --- | --- |
| CaGP | 4.55[1] |
| Calcium Hydroxide | 300–400[1] |
| $CaCO_3$ (from fossil shell) | 4,400[2] |
| $CaCO_3$ (from Dolomite) | 171–315[2] |

[1]Values determined by analysis of commercially available compounds.
[2]Values from Whiting article.

Vitamin D. As used herein and in the claims the terms "vitamin D" and "various forms of vitamin D" are understood to refer to vitamin D, cholecalciferol ($D_3$), ergocalciferol ($D_2$) and its biologically active metabolites and precursors such as, $1\alpha$, 25-$(OH)_2$ vitamin D; 25 OH vitamin D, its biological precursor; and 1x-hydroxyvitamin D, and analogues of the dihydroxy compound. These materials promote intestinal absorption of calcium, contribute to plasma calcium regulation by acting on the remodeling processes of accretion and resorption and stimulate reabsorption of calcium by the kidney. While the form of vitamin $D_3$ used in some of the following examples, is cholecalciferol, it is understood that any of the various forms of vitamin D may be used. Vitamin $D_3$ is preferred in the present invention.

Dietary calcium and vitamin D are the natural mediators against bone loss. Vitamin D acts directly on bone cells (osteoblasts, osteoclasts) to alter bone mass. It also promotes gut uptake of calcium. Human skin activates pre-vitamin D molecules when exposed to ultra violet irradiation.

The optional addition of vitamin D to the liquid nutritional product of the present invention causes some difficulty, as vitamin D is an oil soluble vitamin whereas the beverage of the present invention is an aqueous solution. A number of possible methods to overcome this problem were evaluated.

a. Use of Polysorbate 80 as an Emulsifier

A series of experiments were conducted using vitamin $D_3$ in Polysorbate 80 manufactured to selected specifications by Vitamins Inc., Chicago, Ill., U.S.A. Polysorbate 80 is a water soluble, non-ionic emulsifier used for various applications in the food industry. It is a polyoxyethylene derivative of sorbitan monooleate which interacts with the oil and aqueous phases in an emulsion to form a barrier at the interface that causes a reduction in Van der Waals forces and an improvement in emulsion stability. It was expected that the use of Polysorbate 80 to incorporate the vitamin $D_3$ would improve its recovery and stability by causing dispersion of the oil phase in the continuous aqueous phase.

b. Use of Homogenization

In a series of studies, the vitamin $D_3$/Polysorbate premix was combined with the aqueous phase and the blend was emulsified by passing it through a two-stage Gaulin-L-100 homogenizer at a given pressure. The purpose of this homogenization step is to break up, or evenly disperse, the oil phase into the aqueous phase so that the particle size of the emulsion is sufficiently small to retard coalescence of the oil phase and prevent separation. A two-stage homogenization is needed since the fine particles formed during the first stage can clump. The second stage, set at a lower pressure, is needed to break up the clumps, thereby making a more stable emulsion.

Brominated vegetable oil (BVO) and small quantities of gum arabic were added to the vitamin $D_3$/Polysorbate premix prior to homogenization. This was done to increase the specific gravity of the oil phase and avoid phase separation, or oiling-off, of the emulsion. BVO is used in the soft drink industry as a stabilizer for flavoring oils used in fruit flavored beverages. BVO is a Food Additive (21, CFR 180.30) allowed in an amount not greater than 15 ppm of the finished beverage.

A series of experiments were conducted to evaluate the effect of homogenization on vitamin $D_3$ recovery and stability. All the water soluble components were first dissolved in water and a vitamin $D_3$ emulsion, prepared separately, was added at 1% of finished product concentration, and mixed thoroughly. The vitamin $D_3$ emulsion was prepared by combining water, vitamin $D_3$ and one or more of the following ingredients: Brominated Vegetable Oil (BVO), Polysorbate 80, Gum Arabic (GA), and corn oil, followed by homogenization using a two stage homogenizer. Two different sources of vitamin $D_3$ were used: (a) an oil soluble vitamin premix where the vitamin $D_3$ is dissolved in a small amount of corn oil; and (b) a vitamin $D_3$ premix where the vitamin $D_3$ is dissolved in Polysorbate 80 and propylene glycol (PG). One part of the complete concentrate was then dissolved with five parts of water before carbonation.

The gum arabic used in all batches was Nutriloid Gum Arabic from Tic Gums, Inc.

The initial vitamin $D_3$ Recovery (mean=59.4%) and the mean half-life value (150 days) for these batches indicated that with few exceptions, the homogenization step significantly improved the initial recovery and stability of vitamin $D_3$ versus previous attempts.

The vitamin $D_3$ results from this investigation confirmed that homogenization was necessary when vitamin D was included in the beverage. The mean % Recovery for these batches dramatically improved to 76.7% versus all previous batches.

c. Use of Gum(s) as an Emulsion Stabilizer

The use of gum arabic and gum tragacanth as emulsifying agents for flavor oils in soft drinks is well established in the soft drink industry. Melillo, "Physical Factors Governing the Stabilization of Cloudy Beverages", FOOD PRODUCTS DEVELOPMENT, June, 1977, pp. 108–110. While only gum arabic was used in the experiments, examples and prototypes disclosed herein, it is understood that one skilled in the art could substitute appropriate amounts of gum tragacanth, xanthan gum or any other appropriate gum into the products of the present invention, or that mixtures of gums may be used in the practice of the present invention.

Gum tragacanth is the dried, gummy exudation obtained from *Astragalus gummifer* or other Asiatic species of Astralagus. Tragacanth swells rapidly in either cold or hot water to a viscous colloidal sol or semi-gel. The molecular weight of the gum is on the order of 840,000 and the molecules are elongated (4500 A by 19 A) which accounts for its high viscosity. Tragacanth gum is compatible with other plant hydrocolloids as well as carbohydrates, most proteins, and fats. Viscosity is most stable at pH 4 to 8 with a very good stability down to pH 2.

Xanthan gum is an exocellular heteropolysaccharide produced by a distinct fermentation process. The bacterium *xanthomonas campestris* generates the gum on specific organelles at the cell surface by a complex enzymatic process. The molecular weight for xanthan gum is about two million.

Gum arabic, also known as gum acacia, is the dried, gummy exudate from the stems or branches of *Acacia senegal* or of related species of Acacia. The most unusual property of gum arabic among the natural gums is its extreme and true solubility in cold or hot water.

A series of experiments were conducted to evaluate various types of gum arabic as the emulsifier system in the vitamin $D_3$ emulsion. Although gum arabic had been evaluated in previous experiments, the usage rate was too low (0.14 ppm) to have a significant effect. The amount of gum arabic varied from 100 ppm to 2000 ppm in the finished beverage.

In general it can be said that significant improvements in vitamin $D_3$ stability were observed initially and during shelf-life. The most significant improvement was the stability of vitamin $D_3$ over the shelf life of the product. The average half-life of vitamin $D_3$ for these batches was 180 days. It appears that at sufficient concentration, gum arabic can coat the oil droplets containing the vitamin $D_3$ to form an emulsion that can be further stabilized by homogenization using a two-stage homogenizer.

A series of experiments demonstrated that gum arabic could be substituted for Polysorbate 80 to minimize initial processing loss and improve shelf life stability of vitamin $D_3$.

Acidulants. Acids are commonly used in food and beverages to impart specific tart or sour tastes and to function as preservatives. A combination of citric and lactic acids are used in the liquid nutritional product of the present invention. Citric acid is the most widely used acid in fruit beverages in part because it blends well with these flavors. It is commercially manufactured by fermentation or by synthesis; either may be used in the practice of the present invention. When using fermented lactic acid, a purified form that is free of sugar residues is recommended due to its cleaner taste and clearer appearance. Food grade lactic acid is available in aqueous and crystalline forms.

Sweetener. The sweetener used in the beverages described in the Examples below is aspartame, but other artificial or natural sweeteners can be used in the practice of the present invention. Artificial sweeteners that may be employed include aspartame, saccharin, acesulfame-K and the like. Natural sweeteners that may be employed include sucrose, fructose, high fructose corn syrup, glucose, sugar alcohols, dextrose, maltodextrins, maltose, lactose, and the like but other carbohydrates can be used if less sweetness is desired. Mixtures of natural sweeteners, or artificial sweeteners, or natural and artificial sweeteners can also be used.

The amount of the sweetener effective in a product according to any aspect of the present invention depends upon the particular sweetener used and the sweetness intensity desired. In determining the amount of sweetener, any sugar or other sweetener present in the flavor component or product matrix should also be taken into consideration.

Studies have shown that the efficiency of calcium absorption can be enhanced two-five fold by oral administration of glucose polymer both in patients with intestinal calcium malabsorption and in normal subjects. Kelley, et al., "Effect of Meal Composition on Calcium Absorption: Enhancing Effect of Carbohydrate Polymer" GASTROENTEROLOGY, 87:596–600 (1984).

In another study using the triple-lumen intestinal perfusion technique, glucose polymer increased net calcium absorption fourfold. Bei, et al., "Glucose Polymer Increases and Equal Calcium Magnesium, and Zinc Absorption in Humans", AMERICAN JOURNAL CLINICAL NUTRITION, 44:244–227 (1986).

It is understood that a person of skill in the art may make a product in accordance with the invention containing glucose polymers or glucose.

Ascorbic Acid. Ascorbic acid, also known as vitamin C, is a required element in the beverage of this invention. Vitamin C is a white crystalline compound that is highly soluble in water. The stability of vitamin C decreases with increases in temperature and pH. A considerable quantity of the vitamin C content of foods is lost during processing, storage and preparation. Humans with vitamin C deficiency have what is known as scurvy. They typically lose weight, are easily fatigued, have swollen joints and have fragile bones.

There has been great difficulty is establishing the human requirements for vitamin C. The recommended dietary allowances of the Food and Nutrition Board of the National Research Council are 30 mgs per day for 1–3 month old infants, 80 mgs per day for growing boys and girls, and 100 mgs per day for pregnant and lactating women. Many nutritionists believe that the human intake of ascorbic acid should be many times more than that intake level which produces deficiency symptoms.

Flavor. As used herein, the term "flavor" includes both natural and artificial flavors. The particular amount of the flavor component effective for imparting flavor characteristics to the beverage of the present invention can depend upon the flavor(s) selected, the flavor impression desired, and the form of the flavor component. The amount of flavor employed in a product according to any aspect of the present invention is within the skill of one in the art and depends on the flavor intensity desired.

Preservatives. Most microbial spoilage of low pH beverages is caused by aciduric and acidophilic organisms like certain varieties of yeasts and molds. For this reason, preservatives with anti-microbial activity such as benzoic and sorbic acids are added to soft drinks. Usage levels of these acids or their salts range from 0.025 to 0.050 percent, depending on the nutritive substances present and the pH of the finished beverage. The antimicrobial activity of these preservatives has been shown to be largely pH dependent. They are least effective under neutral conditions but their activity increases considerably with decreasing pH. For example, by reducing the pH value from 4.5 to 3.0, the preservative effect of benzoic acid is increased by nearly three times.

Carbonation. The amount of carbon dioxide in a beverage according to the present invention depends upon the particular flavor system used and the amount of carbonation desired. Usually, carbonated beverages of the present invention contain from 1.0 to 4.5 volumes of carbon dioxide. Preferred carbonated beverages contain from 2 to 3.5 volumes of carbon dioxide. The beverages of the present invention can be prepared by standard beverage formulation techniques. To make a carbonated beverage carbon dioxide can be introduced either into the water mixed with the beverage syrup or into the drinkable diluted beverage to achieve carbonation. It should be understood, however, that carbonated beverage manufacturing techniques, when appropriately modified, are also applicable to noncarbonated beverages.

EMBODIMENTS OF THE INVENTION

Tables 5–8 present bills of materials for manufacturing prototypes of low pH beverages fortified with calcium and vitamin $D_3$ in accordance with some aspects of the invention.

TABLE 5

Bill of Materials for Wild Cherry Flavored Beverage
(For 1000 KG of Beverage)

| INGREDIENT | AMOUNT, KG |
|---|---|
| Treated Water[1] (for beverage concentrate) | 137.82 |
| Potassium Benzoate | 0.300 |
| Sodium Citrate (dihydrate) | 0.550 |
| Citric Acid (anhydrous) | 3.720 |
| Lactic Acid (88%) | 3.951 |
| Aspartame | 0.500 |
| Calcium Glycerophosphate | 8.331 |
| Wild Cherry Color | |
| FD & C Red # 40 | 0.0003465 |
| FD & C Yellow # 6 | 0.0002835 |
| Natural & Artificial Wild Cherry Flavor | 1.200 |
| Ascorbic Acid | 0.300 |
| Vitamin $D_3$ Emulsion | 10.000 |
| Treated Water[1] (for final blend) | 833.33 |

"treated water" has had the chlorine and alkalinity adjusted to levels commonly used in the soft drink industry.

TABLE 6

Bill of Materials for Orange Flavored Beverage
(For 1000 KG of Beverage)

| INGREDIENT | AMOUNT, KG |
|---|---|
| Treated Water[1] (for beverage concentrate) | 137.62 |
| Potassium Benzoate | 0.300 |
| Sodium Citrate (dihydrate) | 0.550 |
| Citric Acid (anhydrous) | 3.720 |
| Lactic Acid (88%) | 3.951 |
| Aspartame | 0.500 |
| Calcium Glycerophosphate | 8.331 |
| Orange Color | |
| FD & C Yellow # 6 | 0.00140625 |
| FD & C Red # 40 | 0.00046875 |
| Natural and Artificial Orange Flavor | 1.400 |
| Ascorbic Acid | 0.300 |
| Vitamin $D_3$ Emulsion | 10.000 |
| Treated Water[1] (for final blend) | 833.33 |

"treated water" had had the chlorine, and alkalinity adjusted to levels commonly used in the soft drink industry.

TABLE 7

Bill of Materials For Peach Flavored Beverage
(For 1000 KG of Beverage)

| INGREDIENT | AMOUNT, KG |
|---|---|
| Treated Water[1] (for beverage concentrate) | 137.42 |
| Potassium Benzoate | 0.300 |
| Sodium Citrate (dihydrate) | 0.550 |
| Citric Acid (anhydrous) | 3.720 |
| Lactic Acid (88%) | 3.951 |
| Aspartame | 0.500 |
| Calcium Glycerophosphate | 8.331 |
| Mohawk Casing Color | |
| FD & C Yellow # 6 | 0.0008125 |
| FD & C Red # 40 | 0.0004375 |
| Natural and Artificial Peach Flavor | 1.600 |
| Ascorbic Acid | 0.300 |
| Vitamin $D_3$ Emulsion | 10.000 |
| Treated Water[1] (for final blend) | 833.33 |

"treated water" has had the chlorine and alkalinity adjusted to levels commonly used in the soft drink industry.

TABLE 8

Bill of Materials For Lemon Lime Flavored Beverage
(For 1000 KG of Beverage)

| INGREDIENT | AMOUNT, KG |
| --- | --- |
| Treated Water[1] (for beverage concentrate) | 138.02 |
| Potassium Benzoate | 0.300 |
| Sodium Citrate (dihydrate) | 0.550 |
| Citric Acid (anhydrous) | 3.720 |
| Lactic Acid (88%) | 3.951 |
| Aspartame | 0.500 |
| Calcium Glycerophosphate | 8.331 |
| Lemon Lime Color | |
| FD & C Yellow # 5 | 0.0005796 |
| FD & C Green # 3 | 0.0000504 |
| Natural and Artificial Lemon Lime Flavor | 1.000 |
| Ascorbic Acid | 0.300 |
| Vitamin $D_3$ Emulsion | 10.000 |
| Treated Water[1] (for final blend) | 833.33 |

"treated water" has had the chlorine and alkalinity adjusted to levels commonly used in the soft drink industry.

EXAMPLE 1

Preparation of Liquid Beverage Concentrate

The concentrated mixture of ingredients that is used to prepare the final beverage is referred to as the beverage concentrate. The liquid beverage concentrate comprises water, a source of calcium, vitamin $D_3$, gum arabic and vegetable oil. Preferably, the beverage concentrate also comprises vitamin C. If desired, the beverage concentrate may also comprise: an acidulant, preservative(s), and/or flavoring agent(s), and/or acid stable coloring agent(s). Prototypes of the beverage of the present invention have calcium levels of about $1.46 \times 10^{-1}$ to about $1.47 \times 10^{-1}\%$ w/w.

In this example the liquid beverage concentrate is prepared in a single vessel at ambient temperature by dissolving the ingredients in water using a blending tank equipped with vigorous agitation capability. A specific order of addition, shown in Table 9, is followed to aid in dispersing the ingredients in an efficient manner. Each ingredient should be completely dissolved before the next ingredient is added.

TABLE 9

1. Water
2. Potassium Benzoate
3. Sodium Citrate
4. Citric Acid
5. Lactic Acid
6. Aspartame
7. Calcium Glycerophosphate
8. Acid Stable Coloring Agent(s)
9. Natural and Artificial Flavor(s) Agent(s)
10. Ascorbic Acid
11. Vitamin $D_3$ Emulsion (vitamin $D_3$ + gum arabic)

In commercial beverage manufacturing, it is common for beverage concentrates to be prepared a day or more (often weeks or months) in advance of blending and filling containers with the final product. For this reason, the vitamin components should be added to the liquid beverage concentrate just prior to blending with water to complete the beverage in order to prevent unnecessary long term exposure to air.

EXAMPLE 2

Preparation of Liquid Beverage Concentrate

Variations to the beverage concentrate manufacturing procedure described in EXAMPLE 1 can be made if available mixing vessel sizes are limited and no single mixing vessel is able to contain the required volume of beverage concentrate. Beverages according to the present invention have been manufactured by preparing a plurality of beverage concentrate component slurries which were thereafter combined by pumping each beverage concentrate component slurry to a larger sized tank. The water was divided equally between five different beverage concentrate component slurries, all of which were constantly agitated. A first beverage concentrate component slurry was made by first adding potassium benzoate and then sodium citrate to the water. A second beverage concentrate component slurry was made by adding to the water in the following order: (a) citric acid; (b) lactic acid: (c) aspartame; (d) calcium glycerophosphate. A third beverage concentrate component slurry was made by adding the acid stable coloring agent(s) and then the flavoring agent(s) to the water. A fourth beverage concentrate component slurry was made by adding the ascorbic acid to the water. A fifth beverage concentrate component slurry was made by adding the vitamin $D_3$ emulsion to the water. The beverage concentrate component slurries are transferred to a single larger sized vessel in the order in which they have been described. The resultant blend (the beverage concentrate) in the larger sized vessel was vigorously agitated for not longer than about two minutes to homogeneously blend the beverage concentrate component slurries together. A liquid beverage concentrate in accordance with the invention should have a pH of 2.8–4.6, preferably 3.1–3.8. The pH of the prototype beverage concentrates typically ranges from 3.1–3.8. If necessary, additional lactic acid is used to adjust the pH of the beverage concentrate to this range.

EXAMPLE 3

Preparation of Carbonated Beverage

Deareation and cooling increases the beverage's carbonation efficiency and stability because the solubility of carbon dioxide in water is directly proportional to carbon dioxide pressure and inversely proportional to temperature. The extent of carbonation is expressed in terms of carbon dioxide gas volumes. The number of volumes can be determined by comparing sample readings with carbon dioxide temperature/pressure relationship charts. Since pressure gauges measure the sum of pressures from all gases, the presence of air in the carbonated mix can cause errors in $CO_2$ volume determination unless corrections are made. A Zahm & Nagel air tester makes it possible to easily measure the pressure and air content of a sample. To make such a test, the sample container is pierced, allowing head space gases to be released into a buret filled with 10–20% sodium or potassium hydroxide. The carbon dioxide is absorbed by the basic solution, leaving only air inside the burette. The total pressure reading is then corrected for the amount of air present in the burette, resulting in the corrected $CO_2$ pressure. The gas volumes of the sample are then determined using the corrected pressure.

A beverage in accordance with the invention may be carbonated by either blending the beverage concentrate with carbonated water or blending the beverage concentrate with water followed by carbonation of the blend. The prototype beverages were manufactured using a 5 to 1 ratio of beverage concentrate manufactured according to Example 2 to non-carbonated water. Carbonation levels in the finished beverage may range from about 1.0–4.5 volumes of $CO_2$, depending on flavor or desired sensory attributes. The product is then packaged and sealed in aluminum cans or tinted glass bottles. During the production of the prototype beverages, separate in-stream lines of beverage concentrate and water were combined in the proper ratio by a continuous metering device known in the art as a volumetric proportioner and then deaerated. The resulting mixture was transferred to a carbo-cooler where it was cooled and carbonated to approximately 2.5 volumes. The pH of the finished beverage should be in the range of about 3.1–4, and the pH of the prototypes was about 3.7. The finished product was then filled into standard 12 oz. aluminum soda cans.

The nutritional profile and initial vitamin $D_3$ Recoveries of the prototype low pH beverages in accordance with the invention are presented in Tables 10 and 11.

TABLE 10

Nutritional Profile Of Prototype Beverage
SERVING SIZE 1 CAN (355 mL)

|  | AMOUNT PER SERVING | % Daily Value* |
|---|---|---|
| Calories | 0 | |
| Total fat | 0 g | 0% |
| Sodium | 45 mg | 2% |
| Potassium | 25 mg | 1% |
| Total Carbohydrate | 0 g | 0% |
| Protein | 0 g | 0% |
| Vitamin C 50% of RDI | | |
| Calcium 50% of RDI | | |
| Vitamin D 30% of RDI | | |

*Not a significant source of other nutrients.
*Percent Daily Values are based on a 2,000 calorie diet.

TABLE 11

Vitamin $D_3$ (IU/Kg Of Product)
(Theoretical Fortification At 810 IU/Kg Of Product)

| FLAVOR | 0-TIME | % RECOVERY |
|---|---|---|
| Cherry | 597 | 73.7 |
| Lemon Lime | 613 | 75.7 |
| Peach | 701 | 86.6 |
| Orange | 580 | 71.6 |

Average = 76.9% vitamin $D_3$ Recovery

EXAMPLE 4

Carbonated Beverage

An alternative embodiment of a liquid beverage concentrate may be prepared according to Example 1 or Example 2 excluding any ingredients other than the water, calcium source, vitamin $D_3$ emulsion (e.g., the flavorant, and/or the colorant, and/or the sweetener may be omitted). This liquid beverage concentrate may then be combined with another liquid beverage concentrate, such as a commercial soda pop concentrate, and the resultant blended beverage concentrate may thereafter be combined with carbonated water, or combined with non-carbonated water with the resultant beverage being carbonated in the manner described above in Example 3.

EXAMPLE 5

Non-Carbonated Beverage

A liquid beverage concentrate may be prepared by blending a liquid beverage concentrate according to the present invention, such as described above in Examples 1 and 2, with non-carbonated water. The resultant blend could then be placed into aluminum soda cans, or light reducing bottles, the head space flushed with nitrogen gas or carbon dioxide to eliminate oxygen which is harmful to vitamin and color stability, and sealing the cans in the usual manner.

EXAMPLE 6

Non-Carbonated Beverage

An alternative embodiment of a liquid beverage concentrate may be prepared according to Example 1 or Example 2 excluding any ingredients other than the water, calcium source and vitamin $D_3$ emulsion (e.g. the flavorant, and/or colorant, and or sweetener could be omitted), and thereafter blending the concentrate with fruit juice, vegetable juice, or any other suitable liquid matrix.

EXAMPLE 7

Powdered Beverage Concentrate

The bill of materials for a powdered beverage concentrate in accordance with the invention is presented in Table 12.

TABLE 12

Bill Of Materials For Powdered Beverage Concentrate

| INGREDIENT | AMOUNT |
|---|---|
| Vitamin $D_3$ Emulsion | 350 g |
| Calcium Clycerophosphate | 291.6 g |
| Lactic Acid Powder (60% lactic acid) | 181.3 g |
| Citric Acid | 130.2 g |
| Natural Cherry Flavor | 42.0 g |
| Sodium Citrate Dihydrate | 19.3 g |
| Aspartame | 17.5 g |
| Ascorbic Acid | 10.5 g |

A powdered beverage concentrate was prepared by placing the calcium glycerophosphate, sodium citrate, citric acid, lactic acid and ascorbic acid into the chamber of an Aeromatic Top Agglomerator. The powder was then blended for two minutes under medium fluidization. The temperature was brought to 70° C., the atomization was set at 1 Bar, the atomizing nozzle was placed at the highest level of three possible positions, and the fan capacity was set initially at 12 (nominal setting).

Aspartame was dissolved in approximately 800 ml of warm tap water and a small amount of citric acid was added to achieve a pH of approximately 4. The vitamin $D_3$ emulsion and the flavor system were blended by hand with the aspartame solution to yield approximately 1200 ml of liquid. The 1200 ml of liquid was placed on a stir plate and agitated under medium agitation while being sprayed onto the fluidized powder for approximately three hours.

As the liquid was sprayed, the powder became heavy and it became necessary to increase the fan capacity to maximum and place the atomizing nozzle in the center position. Per actual analysis, a Kg of powdered beverage concentrate contained about 83.5 g of calcium, 12.9 g of vitamin C and 31,900 IU of vitamin $D_3$.

The final powder particles were relatively large and brittle and were pulverized before reconstituting with water. The powder was easily reconstituted (see Example 8) and flavor was typical of a powdered beverage concentrate product without the carbonation. Longer shelf life in this kind of beverage concentrate is anticipated because of the absence of water.

EXAMPLE 8

Non-Carbonated Beverage Containing Powdered Beverage Concentrate

Approximately 19.1 grams of the powdered beverage concentrate manufactured in Example 7 were dissolved in a sufficient amount of tap water to yield 1 Kg of beverage. A Kg of the resultant beverage is projected to contain about 1.6 g of calcium, about 0.25 g of vitamin C, and about 607 IU of vitamin $D_3$. As in the case of the liquid form of the powdered beverage concentrate, the acid system can vary depending on the flavor selected.

EXAMPLE 9

Powdered Beverage Additive

A powdered beverage additive may be manufactured by the process described in Example 7, containing at least vitamin $D_3$ emulsion, a calcium source and vitamin C, but if desired omitting sweetener, acids, flavoring, etc. The resultant powdered beverage additive could be added in appropriate quantities to a liquid matrix such as a fruit juice, blend of fruit juices, vegetable juice, coffee, tea or any suitable beverage. The powdered beverage additive could be employed in bulk, (e.g. at an orange juice processing facility), or on a serving by serving basis when provided in single serving size packets.

It should be noted that if a liquid or powdered beverage concentrate or beverage additive according to the invention is intended for use in a liquid matrix that may contain any dairy product, (for example, coffee or tea that may contain cream), a salt of ascorbic acid such as calcium and sodium ascorbate should be used in place of ascorbic acid to prevent curdling of the dairy product.

EXAMPLE 10

Calcium Supplement

A calcium glycerophosphate/vitamin $D_3$/vitamin C tablet supplement was prepared by placing about 291.6 g of calcium glycerophosphate and about 10.5 g of ascorbic acid (vitamin C) into the chamber of an Aeromatic laboratory batch agglomerator. The powder was then blended for three minutes under medium agitation. The temperature was brought to 55° C., the atomization was set to 1 bar, the atomizing nozzle was placed at the highest of three possible positions, and the fan capacity was set initially at 9 (nominal setting).

The peristaltic pump was set at 7 cc/minute and approximately 350 g of vitamin $D_3$ emulsion was sprayed onto the fluidized powder. The commercially manufactured vitamin $D_3$ emulsion described above with respect to batch 31 was used in this calcium supplement. However, any suitable dry blendable source of vitamin D, preferably vitamin $D_3$ or $D_2$, may be used for making a solid calcium supplement according to the invention. As the liquid emulsion was sprayed, the powder became heavy and as powder fluidization was depressed the fan speed was incrementally increased to 12 over 55 minutes to maintain medium fluidization. Temperature was also increased to 60° C. after 16 minutes. After all the vitamin $D_3$ emulsion was sprayed on the powder, the heat was kept on and the powder was dried for three minutes. Per actual analysis, a Kg of powder for tableting contained about 139.9 g of calcium, 26.4 g of vitamin C, and 39,600 IU of vitamin $D_3$.

The final powder particle was a soft agglomerate. No excipients were added to the powder to facilitate the tableting process. Using a tablet die of approximately ½ inch diameter, 600 g of the final powder was compressed using a Carver model C laboratory press and an applied load of 200 pounds force. The tablet was easily removed from the die. This process was repeated using 1000 g and 1500 g of final powder to produce a total of three calcium supplement tablets, 600 g, 1000 g, and 1500 g, respectively.

The solid supplement of this Example contained about 1.1% by wt. vegetable oil as calculated from the amount of vitamin D emulsion added to the CaGP powder and the amount of oil in the emulsion. One skilled in the art will appreciate that higher levels of vegetable oil, for example up to 5 wt. %, would be possible without detracting from the inventive supplement's ability to be tableted. Those skilled in the preparation of emulsions, such as the vitamin D emulsion, will understand that higher levels of oil will require higher levels of the gums which stabilize the emulsion. Thus, the solid calcium supplement of this invention comprises CaGP, vitamin D, vegetable oil at less than 5% by wt. more preferably from 105% by wt. and most preferably at about 1% by wt.

A calcium supplement in solid form in accordance with the invention, comprising calcium glycerophosphate, vitamin D, and vitamin C, is believed to be advantageous over prior art calcium supplements because it provides a source of calcium that has a low aluminum content as well as providing vitamin D.

EXAMPLE 11

Organoleptic Testing

This experiment was conducted to evaluate the impact of various sources of calcium on the taste of the final beverage. Using a procedure similar to that set out in Example 3 above, beverages were prepared using calcium sources as set out in Table 13. Table 13 also sets out the amount of calcium in each beverage, the level of aspartame, the pH of the resulting beverages and the titratable acidity of each beverage.

TABLE 13

| Beverage No. | Mineral Source | Calcium mg/ 100 g | Aspartame mg/L | pH (2 runs) | Titratable Acidity (ml of 0.1 N NaOH to reach pH 8.3) (avg. of 2 runs) |
|---|---|---|---|---|---|
| 1 | calcium lactate | 110 | 529 | 3.68 | 29.2 |
|   |   |   |   | 3.81 | 29.0 |
| 2 | calcium gluconate | 99 | 528 | 3.87 | 25.7 |
|   |   |   |   | 3.87 | 25.0 |
| 3 | calcium citrate malate | 103 | 531 | 3.88 | 36.6 |
|   |   |   |   | 3.58 | 36.4 |
| 4 | calcium glycerophosphate | 105 | 532 | 3.85 | 34.3 |
|   |   |   |   | 3.67 | 34.6 |

The beverages of Table 13 provide about 33% of the RDI for calcium in a 12 oz. serving. Each beverage was evaluated for Fullness, Balance, Sweet, Sour and Aftertaste by a panel of individuals trained in sensory evaluation.

Balance is a measure of the degree of blend or the balance of the character notes in the beverage. Balance is affected by the intensities of the character notes as well as the order of appearance of the notes. It is rated on a scale of one (unblended) to seven (blended).

Fullness refers to the fullness and body of flavor or the degree of complexity. It is rated on a scale of one (thin) to seven (full).

Sweet is a measure of the level of sweet basic taste. The reference standard for sweet intensity, measured on a scale from one to seven, is sucrose solutions of 5% for slight (3), 10% for moderate (5), and 15% for strong (7).

Sour is a measure of the level of sour basic taste. The reference standard for sour intensity, measured on a scale from one to seven, is citric acid solutions of 0.05% for slight (3), 0.10% for moderate (5), and 0.20% for strong (7).

Aftertaste is a measure of all sensations remaining one minute after swallowing. This is measured on a scale of one (none) to seven (strong). This includes basic tastes, feeling factors, and aromatics. The panelists recorded the character notes in their comments.

Of all the profiles, Balance is the most important and is generally regarded as the most pertinent measure of a beverage's consumer acceptance. All beverages were evaluated chilled (about 10° C.).

The results of this investigation are set forth in Table 14.

TABLE 14

Organoleptic Evaluations
(Values Reported Are Averages From The Panel)

| Beverage No. | Fullness | Balance | Sweet | Sour | Aftertaste |
|---|---|---|---|---|---|
| 1-calcium lactate | 3.6 | 3.6 | 4.3 | 4.3 | 2.7 |
| 2-calcium gluconate | 3.0 | 2.0 | 4.5 | 2.5 | 4.3 |
| 3-calcium citrate malate | 3.3 | 3.6 | 4.0 | 4.3 | 3.0 |
| 4-CaGP | 3.8 | 4.3 | 4.0 | 4.2 | 2.7 |

This investigation demonstrates that calcium glycerophosphate is the preferred source of calcium from a taste perspective. With reduced aftertaste and high levels of balance, the use of CaGP provides a highly acceptable liquid composition for supplying at least 30%, more preferably 50% and most preferably 100% of the RDI for calcium in a 12 oz. serving.

Beverage No. 2 (calcium gluconate) stood out among the samples as the most different. It had the lowest balance score, which was due to a high mineral salt and phenolic off-notes. Even though Beverage No. 2 was less sour than the other beverages, this did not improve the Balance or Fullness because the off-note was so noticeable.

EXAMPLE 12

Calcium Fortified Beverage without Vitamin D

One aspect of this invention resides in the use of CaGP and acidulants to produce a beverage that will supply at least 30%, more preferably 50% and most preferably 100% of the RDI for calcium in one twelve ounce serving. In one embodiment of this invention, the beverage contains no vitamin D as the use of this vitamin requires the presence of emulsifiers which complicate the manufacture of the beverage.

To produce a 1000 kg batch of ready-to-drink beverage, 987.31 kg of water was placed in a vessel fitted with an agitator. At ambient temperature, 0.30 kg of potassium benzoate was added and allowed to completely dissolve. The following ingredients were then added in the order listed. Each ingredient was completely dissolved before the next ingredient was added.

| | |
|---|---|
| Potassium Citrate | 0.15 kg |
| Citric Acid | 2.89 kg |
| Lactic Acid | 1.41 kg |
| Aspartame | 0.55 kg |
| Calcium Glycerophosphate | 6.06 kg |
| Coloring Agents | 0.0019 kg |
| Natural and artificial flavors | 1.00 kg |
| Ascorbic acid | 0.33 kg |

The ascorbic acid was added just before filling into 12 oz. aluminum cans.

EXAMPLE 13

An alternative method to the single vessel method set forth in Example 12 is the "addition of slurries" method. In the "addition of slurries" method, four slurries are prepared in separate vessels an then combined to form the final beverage. This approach is more practical than making one large batch, and is the preferred method of preparation.

Four slurries were made using the ingredients and amounts set forth in Example 12, except that the water was divided equally between the four vessels. Each ingredient was allowed to dissolve prior to the addition of the next ingredient.

| | | |
|---|---|---|
| Slurry #1 | 1) | potassium benzoate |
| | 2) | potassium citrate |
| Slurry #2 | 1) | citric acid |
| | 2) | lactic acid |
| | 3) | aspartame |
| | 4) | calcium glycerophosphate |
| Slurry #3 | 1) | coloring agents |
| | 2) | natural and artificial flavors |
| Slurry #4 | 1) | ascorbic acid |

Each slurry was pumped to a larger tank and the resulting blend was well mixed. Slurry #4, with the ascorbic acid, was added about 2 minutes before carbonation.

EXAMPLE 14

The beverages prepared in Example 12 and 13 were carbonated prior to filling into aluminum cans. The solutions were de-aerated and then transferred to a "carbo-cooler" where they were cooled and carbonated to approximately 2.5 volumes of carbon dioxide.

EXAMPLE 15

Beverage Concentrate or Syrup

Using the ingredients and amounts set forth in Example 12, except that 16.7% by weight of water was used, a beverage syrup was prepared using the one vessel method. Each ingredient was completely dissolved prior to the addition of the next ingredient.

Using the procedure set forth in Example 13, a beverage syrup was made, except that 16% by weight of the recited amount of water was divided between the four vessels.

Preparation of the final beverage was accomplished through blending the syrup with water at a 1 to 5 ratio using a continuous metering device called a volumetric proportioner.

EXAMPLE 16

Beverage with 50% of RDI for Calcium and Vitamin C

In this experiment a low pH, non-caloric, carbonate beverage was prepared using Diet 7Up® concentrate mix as the base. The following ingredients were combined in the order listed. Each ingredient was completely dissolved before the next ingredient was added.

| INGREDIENT | AMOUNT |
|---|---|
| Water | 9.93 Kg |
| Diet 7Up ® Concentrate | 1.8 Kg |
| CaGP | 129 g |
| Ascorbic Acid | 1.48 g |
| Acid Solution | 60 ml |

The acid solution consisted of 24.4 g of 50% by wt. citric acid, 25.4 g of 75% phosphoric acid by wt. and 50.2 g of 85% lactic acid by wt. The mixture was placed in a carbonation cylinder and cooled to about 1°–2° C. Carbon dioxide was then injected to approximately 3 volumes. 8 oz (240 ml) bottles were filled and capped. The beverage was clear and colorless. The CaGP was extremely soluble in this matrix and did not precipitate or cause any negative flavor notes. This beverage contained about 50% of the RDI for calcium and about 100% vitamin C in one serving (12 oz).

We claim:

1. A liquid beverage consisting essentially of:
   a. water;
   b. calcium glycerophosphate at a concentration of 1.77–5.91 g/355 ml;
   c. vitamin C at a concentration of at least 18 mg/355 ml;
   d. sweeteners;
   e. flavoring agents; and
   f. an acidulant, said beverage having a pH in the range of about 2.8 to 4.6.

2. A liquid beverage comprising:
   a. water;
   b. calcium glycerophosphate at a concentration of 1.77–5.91 g/355 ml;
   c. vitamin D;
   d. vegetable oil;
   e. a non-hydrolyzed gum selected from the group consisting of gum arabic, gum tragacanth and xanthan gum; and
   f. vitamin C at a concentration of at least 18 mg/355 ml; and
   g. an acidulant, said liquid beverage having a pH in the range of about 2.8 to 4.6.

3. The liquid beverage according to claim 2 wherein the vitamin D is vitamin D3; the vegetable oil is selected from the group consisting of corn oil and partially hydrogenated soybean oil; the gum is gum arabic and acidulant is citric acid.

4. A liquid beverage as described in claim 3 further comprising citric and lactic acid as acidulants.

5. A liquid beverage as described in claim 3 further comprising potassium benzoate.

6. A liquid beverage as described in claim 3 further comprising a flavoring agent.

7. A liquid beverage as described in claim 3 further comprising a sweetener.

8. A liquid beverage as described in claim 3 further comprising a flavoring agent and aspartame as the sweetener.

9. A liquid beverage comprising:
   a. water;
   b. calcium glycerophosphate at a concentration of 1.77–5.91 g/355 ml;
   c. vitamin C at a concentration of at least 18 mg/355 ml; and
   d. acidulants, wherein the said acidulants are a mixture comprising lactic acid and citric acid.

10. A liquid beverage according to claim 9 further comprising a glucose polymer.

11. A liquid beverage as described in claim 9 further comprising at least 338 IU of vitamin D per 355 ml of beverage.

12. A liquid beverage as described in claim 9 wherein the beverage is carbonated.

* * * * *